(12) United States Patent
Moser et al.

(10) Patent No.: US 12,048,700 B2
(45) Date of Patent: *Jul. 30, 2024

(54) CRYSTALLINE MONOSODIUM SALT OF 5-METHYL-(6S)-TETRAHYDROFOLIC ACID

(71) Applicant: Merck Patent GmbH, Darmstadt (DE)

(72) Inventors: Rudolf Moser, Schaffhausen (CH); Viola Groehn, Dachsen (CH); Fritz Blatter, Reinach (CH); Martin Szelagiewicz, Basel (CH); Ruth Boehni Stamm, Stein Am Rhein (CH); Markus Ruettimann, Winterthur (CH); Giuseppe Lapadula, Basel (CH)

(73) Assignee: MERCK PATENT GMBH, Darmstadt (DE)

( * ) Notice: Subject to any disclaimer, the term of this patent is extended or adjusted under 35 U.S.C. 154(b) by 70 days.

This patent is subject to a terminal disclaimer.

(21) Appl. No.: 17/387,077

(22) Filed: Jul. 28, 2021

(65) Prior Publication Data

US 2022/0016121 A1    Jan. 20, 2022

Related U.S. Application Data

(63) Continuation of application No. 16/498,549, filed as application No. PCT/EP2018/057900 on Mar. 28, 2018, now Pat. No. 11,185,545.

(30) Foreign Application Priority Data

Mar. 31, 2017   (EP) ..................... 17164349

(51) Int. Cl.
*A61K 31/519*    (2006.01)
*C07D 475/04*   (2006.01)
*C07D 487/04*   (2006.01)

(52) U.S. Cl.
CPC .......... *A61K 31/519* (2013.01); *C07D 487/04* (2013.01); *C07B 2200/13* (2013.01)

(58) Field of Classification Search
CPC ........................ A61K 31/519; C07D 475/04
USPC ...................... 514/262.1; 544/258
See application file for complete search history.

(56) References Cited

U.S. PATENT DOCUMENTS

| | | | |
|---|---|---|---|
| 5,124,452 A | | 6/1992 | Gennari |
| 5,538,734 A | | 7/1996 | Le Grazie |
| 5,719,045 A | | 2/1998 | Heveling et al. |
| 5,817,659 A | | 10/1998 | Muller et al. |
| 6,011,040 A | * | 1/2000 | Muller .............. A61P 9/10 |
| | | | 514/250 |
| 6,441,168 B1 | | 8/2002 | Muller et al. |
| 6,596,721 B2 | | 7/2003 | Müller et al. |
| 9,150,982 B2 | | 10/2015 | Wang et al. |
| 2015/0004300 A1 | | 1/2015 | Cavalieri Manasse |
| 2016/0207925 A1 | | 7/2016 | Fracchia |

FOREIGN PATENT DOCUMENTS

| | | |
|---|---|---|
| CN | 104557937 B | 3/2017 |
| EA | 017742 B1 | 2/2013 |
| RU | 2165422 C2 | 4/2001 |
| RU | 2187508 C2 | 8/2002 |
| WO | 13025203 A1 | 2/2013 |
| WO | 13050960 A1 | 4/2013 |
| WO | 2015/193778 A1 | 12/2015 |

OTHER PUBLICATIONS

Jordan, V. C. Nature Reviews: Drug Discovery, 2, 2003, 205.*
Dorwald, F. Zaragoza. Side Reactions in Organic Synthesis: A Guide to Successful Synthesis Design, Weinheim: WILEY-VCH Verlag Gmbh & Co. KGaA, 2005, Preface.*
Vippagunta, et al. Advanced Drug Delivery Reviews, 48, 2001, 18.*
International Search Report dated Jun. 4, 2018 issued in corresponding PCT/EP2018/057900 application (4 pages).
M. Caira, "Crystalline Polymorphism of Organic Compounds", Topics in Current Chemistry, vol. 198 (1998) pp. 163-208.
Office Action in corresponding CN 201880020919.3 dated Jan. 6, 2022 (pp. 3-10).
Office Action in corresponding Japanese Patent Application No. 2019-553824 dated Mar. 22, 2022 (pp. 3-10).
Hirayama Noriaki, Organic Compound Crystal Fabrication Handbook; 2008; pp. 17-23, 37-40, 45-51, 57-65.
Kawaguchi Yoko et al., Pharmaceuticals and crystallographic polymorphism, Life-Engineering Studies, 2002, vol. 4, No. 2, pp. 310-317.
Balbach et al., "Pharmaceutical evaluation of early development candidates "the 100 mg-approach"" International Journal of Pharmaceutics, 2004, 275, 1-12.
Singhal et al., "Drug polymorphism and dosage form design: a practical perspective" Advanced Drug Delivery Reviews, 2004, 56, 335-347.
Berstein, J., „Polimorfizm molekulârnyh kritallov [Polymorphism in Molecular Crystals] Moscow: Nauka, 2007, Ch. 7.3.2 "Bioavailability", 324-330.

(Continued)

*Primary Examiner* — Douglas M Willis
(74) *Attorney, Agent, or Firm* — MILLEN, WHITE, ZELANO & BRANIGAN, P.C.; Csaba Henter (57) ABSTRACT

Crystalline monosodium salt of 5-methyl-(6S)-tetrahydrofolic acid wherein the molar ratio of 5-methyl-(6S)-tetrahydrofolic acid to sodium is from 1:0.5 to 1:1.5 (in mol/mol) and/or hydrates and/or solvates thereof, their use as pharmaceuticals, as well as processes of obtaining the same.

22 Claims, 5 Drawing Sheets

(56) References Cited

OTHER PUBLICATIONS

Kummerer, K., "Pharmaceuticals in the Environment" Annual Review of Environment and Resources, 2010, 35, 57-75.
Morissette Sherry L. et al., "High-throughput crystallization: polymorphs, salts, co-crystals and solvates of pharmaceutical solids" Advanced Drug Delivery Reviews, 2004, 56, 275-300.
Kuznecova G. A., Methodical guidelines, Irkutsk State University, Chair for General Physics, 2005, p. 3 par. 2.
Rodriguez-Spong et al., "General principles of pharmaceutical solid polymorphism: A supramolecular perspective" Advanced Drug Delivery Reviews, 2004, 56, 241-274.
Maškovskij, M. D., Lekarstvennye sredstva [Medicaments] 14th ed., vol. 1, Moscow: Novaâ volna, 2001, p. 11.
English tranlation of Search report in corresponding Russian application dated Jul. 21, 2021 (pp. 1-16).
Byrn S. et al.: Pharmaceutical Solids: A Strategic Approach to Regulatory Considerations, Review, Pharmaceutical Research, vol. 12, No. 7, 1995, pp. 945-954.
Knunânc I. L. (Ed.) Himičskij enciklopedičeskij slovar' [Encyclopedia of Chemistry]. Moscow: Sovetskaâ Enciklopediâ, 1983, pp. 130-131.
Harkevič D.A. Farmakologiâ [Pharmacology] (10th ed.), Moscow: GEOTAR-Media, 2010, pp. 73-74.
Office action in corresponding Russian Patent Application No. 2019 133 594 dated Jan. 16, 2023 (pp. 1-21) an English translation thereof (pp. 1-21).

\* cited by examiner

Fig. 1: PXRD of crystalline monosodium salt of 5-methyl-(6S)-tetrahydrofolic acid according to Example 1

Fig. 2: Properties on drying of monosodium salt of 5-methyl-(6S)-tetrahydrofolic acid Fig. 3: Properties of calcium salt of 5-methyl-(6S)-tetrahydrofolic acid (reference)

Fig. 4: Variable water content under changing relative humidity conditions of monosodium salt of 5-methyl-(6S)-tetrahydrofolic acid Fig. 5: Properties of calcium salt of 5-methyl-(6S)-tetrahydrofolic acid (reference)

Fig. 6: Fingerprint region of FT-Raman spectrum of the crystalline monosodium salt of 5-methyl-(6S)-tetrahydrofolic acid according to Example 1 in the wavenumber range from 200 to 1800 cm$^{-1}$ Fig. 7: Long-term stability of the crystalline monosodium salt of 5-methyl-(6S)-tetrahydrofolic acid at 25°C/60%rh (% w/w)

Fig. 8: Long-term stability of the crystalline monosodium salt of 5-methyl-(6S)-tetrahydrofolic acid at 25°C/60%rh (major degradation product [MeFox]) (% w/w)

Fig. 9: Long-term stability of the crystalline monosodium salt of 5-methyl-(6S)-tetrahydrofolic acid at 40°C/75%rh (% w/w)

Fig. 10: Long-term stability of the crystalline monosodium salt of 5-methyl-(6S)-tetrahydrofolic acid at 40°C/75%rh (major degradation product [MeFox]) (% w/w)

CRYSTALLINE MONOSODIUM SALT OF 5-METHYL-(6S)-TETRAHYDROFOLIC ACID

The present invention is directed to a crystalline sodium salt of 5-methyl-(6S)-tetrahydrofolic acid, (N-[4-[[(2-amino-1,4,5,6,7,8-hexahydro-5-methyl-4-oxo-(6S)-pteridinyl)methyl]amino]benzoyl]-L-glutamic acid, herein abbreviated as MTHF, and a process of obtaining the same.

Tetrahydrofolates are predominantly used as 5-formyltetrahydrofolic acid and the salts thereof (leucovorin and levoleucovorin), as 5-methyltetrahydrofolic acid and the salts thereof (Metafolin®), or as 5,10-methylenetetrahydrofolic acid and the salts thereof (Modufolin®) for the treatment of megaloblastic folic acid anaemia, as an antidote for increasing the compatibility of folic acid antagonists, particularly of aminopterin and methotrexate in cancer therapy ("antifolate rescue"), for increasing the therapeutic effect of fluorinated pyrimidines and for the treatment of autoimmune diseases such as psoriasis and rheumatoid arthritis, for increasing the compatibility of certain antiparasitic for mutations, for instance trimethoprim-sulfamethoxazole, and for reducing the toxicity of dideazatetrahydrofolates in chemotherapy.

5-Methyltetrahydrofolic acid is used in particular as a drug and as a food additive, as a vitamin preparation, for the prevention of neural tube defects, for the treatment of depressive illnesses, and for influencing the homocysteine level.

5-Methyltetrahydrofolic acid and salts thereof are extremely unstable and in particular are highly susceptible to oxidation [see also A. L. Fitzhugh, Pteridines 4 (4), 187-191 (1993) in this respect] and are therefore difficult to produce at a level of purity which is acceptable for a pharmaceutical active ingredient or a food additive.

Various methods, such as excluding oxygen as completely as possible or the addition of antioxidants such as ascorbic acid or reduced L-glutathione, have been employed in order to overcome the instability of 5-methyltetrahydrofolic acid.

U.S. Pat. No. 6,441,168 B1 discloses alkaline earth salts of 5-methyltetrahydrofolic acid, particularly the calcium salt, its crystallization and its use. The crystalline calcium salt of 5-methyl-(6S)-tetrahydrofolic acid exists in four different crystalline modifications. The drawback of the calcium salt of 5-methyl-(6S)-tetrahydrofolic acid is that it exists in four modifications, since the process of manufacturing each of which has to be controlled very precisely. Additionally, the solubility of said calcium salt of 5-methyl-(6S)-tetrahydrofolic acid in water is relatively poor, possibly leading to a reduced bioavailability and a limitation to its applicable form of use. Also a low solubility is resulting in low time-volume yields when needing to dissolve such compound for further processing e.g. a purification by recrystallization. Additionally the crystalline salts of 5-methyl-(6S)-tetrahydrofolic acid of U.S. Pat. No. 6,441,168 B1 also are having a water of crystallization of at least one equivalent per equivalent of 5-methyltetrahydrofolic acid.

New crystal forms of a pharmaceutically useful compound offer an opportunity to improve the performance profile of a pharmaceutical and/or vitamin/medical food products. It widens the reservoir of materials a formulation scientist has available for designing new dosage forms with improved characteristics.

The technical problem underlying the present invention is the provision of a crystalline form comprising 5-methyl-(6S)-tetrahydrofolic acid which overcomes the drawbacks of the crystalline calcium salt of 5-methyl-(6S)-tetrahydrofolic acid known in the art.

Additionally, new crystalline forms often show desired different physical and/or biological characteristics, which may assist in the manufacture or formulation of the active compound, to the purity levels and uniformity required for regulatory approval.

For the sake of stability of the reduced folates it is always the aim to provide a compound which has a low water absorption upon storage and which can be dried sufficiently during manufacturing.

The technical problem is solved by a crystalline sodium salt of 5-methyl-(6S)-tetrahydrofolic acid wherein the molar ratio of 5-methyl-(6S)-tetrahydrofolic acid to sodium is from 1:0.5 to 1:1.5 (in mol/mol) and/or hydrates and/or solvates thereof.

The solid form of the present invention possesses improved pharmacological characteristics, for example, improved bioavailability, thus offering enhanced possibilities to modulate and design improved drug products.

Additionally, only one crystalline modification of sodium salt of 5-methyl-(6S)-tetrahydrofolic acid exists, thus, leading to an improved process of obtaining the same.

Even further the crystalline sodium salt of 5-methyl-(6S)-tetrahydrofolic acid of the present invention shows unexpectedly superior long-term stability when compared to the previously known crystalline calcium salt of 5-methyl-(6S)-tetrahydrofolic acid. The improved stability of the crystalline sodium salt of 5-methyl-(6S)-tetrahydrofolic acid of the present invention could lead to an increased shelf life, less stringent storage conditions and/or more convenient/expensive prerequisites over the supply chain.

Additionally the crystalline sodium salt of 5-methyl-(6S)-tetrahydrofolic acid of the present invention shows an increased solubility and especially an increased kinetic solubility against 5-methyl-(6S)-tetrahydrofolic acid and respective salts thereof known in the state of the art. The increased solubility and especially an increased kinetic solubility of the crystalline sodium salt of 5-methyl-(6S)-tetrahydrofolic acid of the present invention could lead to different processing parameters such as e.g. shorter dissolution times and thereby less oxidative stress to the product and/or finally even other application forms such as rapidly soluble powders.

Preferably, the crystalline salt has a molar ratio of 5-methyl-(6S)-tetrahydrofolic acid to sodium from 1:0.75 to 1:1.25 (in mol/mol).

In a further preferred embodiment the crystalline salt has a molar ratio of 5-methyl-(6S)-tetrahydrofolic acid to sodium of approximately 1:1 (in mol/mol).

Preferably, the crystalline salt of the present invention is the sodium salt of 5-methyl-(6S)-tetrahydrofolic acid and has a PXRD pattern with at least one characteristic peak (expressed in 2θ±0.2° 2θ (CuKα radiation)) at 6.5, 10.2, 13.1, 15.3, 17.9, 20.5, and 22.0.

Even more preferred, the crystalline salt of the present invention is the sodium salt of 5-methyl-(6S)-tetrahydrofolic acid and has a PXRD pattern with at least two, even more preferred at least three, most preferred at least four, preferably at least five, more preferred at least six and most preferred all of the characteristic peaks (expressed in 2θ±0.2° 2θ (CuKα radiation)) at 6.5, 10.2, 13.1, 15.3, 17.9, 20.5, and 22.0.

Even more preferred, the crystalline salt of the present invention is the sodium salt of 5-methyl-(6S)-tetrahydrofolic acid and has a PXRD pattern with at least one characteristic peak (expressed in 2θ±0.2° 2θ (CuKα radiation)) at 6.5, 10.2, 12.5, 13.1, 14.8, 15.1, 15.3, 16.1, 17.2, 17.9, 20.4, 20.5, 21.2, 22.0, 22.5, and 27.2.

Figure 1:
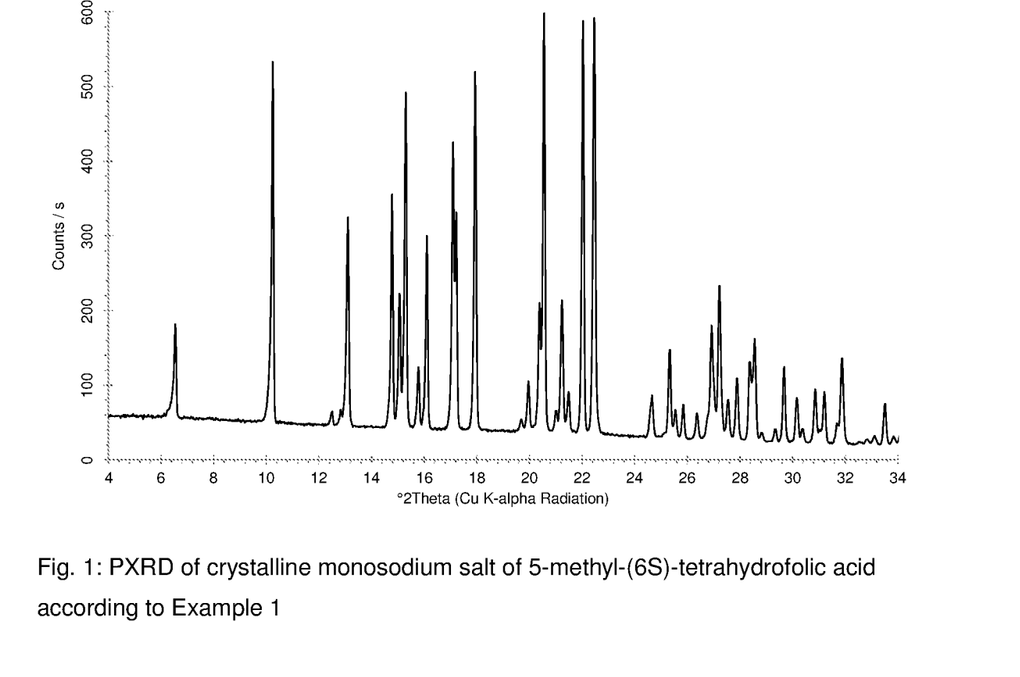
FIG. 1 shows PXRD of crystalline monosodium salt of 5-methyl-(6S)-tetrahydrofolic acid according to Example 1.

Preferably, the crystalline salt of the present invention is the sodium salt of 5-methyl-(6S)-tetrahydrofolic acid and has a PXRD pattern with at least two, even more preferred at least three, most preferred at least four, preferably at least five, more preferred at least six and most preferred all of the characteristic peaks (expressed in 2θ±0.2° 2θ (CuKα radiation)) at 6.5, 10.2, 12.5, 13.1, 14.8, 15.1, 15.3, 16.1, 17.2, 17.9, 20.4, 20.5, 21.2, 22.0, 22.5, and 27.2 and most preferred has a PXRD pattern substantially as shown in FIG. 1.

Preferably, the crystalline sodium salt of 5-methyl-(6S)-tetrahydrofolic acid is a crystalline monosodium salt of 5-methyl-(6S)-tetrahydrofolic acid.

Even more preferred, the water content of the crystalline sodium salt of 5-methyl-(6S)-tetrahydrofolic acid is less than 5 wt-%, preferably less than 3 wt-%, more preferably less than 1 wt-%. Especially preferred is the crystalline sodium salt of 5-methyl-(6S)-tetrahydrofolic acid an anhydrous crystalline sodium salt of 5-methyl-(6S)-tetrahydrofolic acid and most preferred an anhydrous crystalline monosodium salt of 5-methyl-(6S)-tetrahydrofolic acid.

A further aspect of the invention is the crystalline sodium salt of 5-methyl-(6S)-tetrahydrofolic acid having a Raman spectrum with least one characteristic peak (expressed in wavenumbers, cm$^{-1}$, with an experimental uncertainty of ±1-2 cm$^{-1}$) at: 3079, 3036, 2991, 2962, 2941, 2927, 2902, 2852, 1674, 1608, 1570, 1527, 1483, 1466, 1446, 1415, 1321, 1302, 1274, 1243, 1224, 1193, 1168, 1059, 1019, 947, 898, 854, 810, 775, 648, 637, 510, 479, 415, 378, 284, 260 and 196 cm$^{-1}$.

Figure 6:
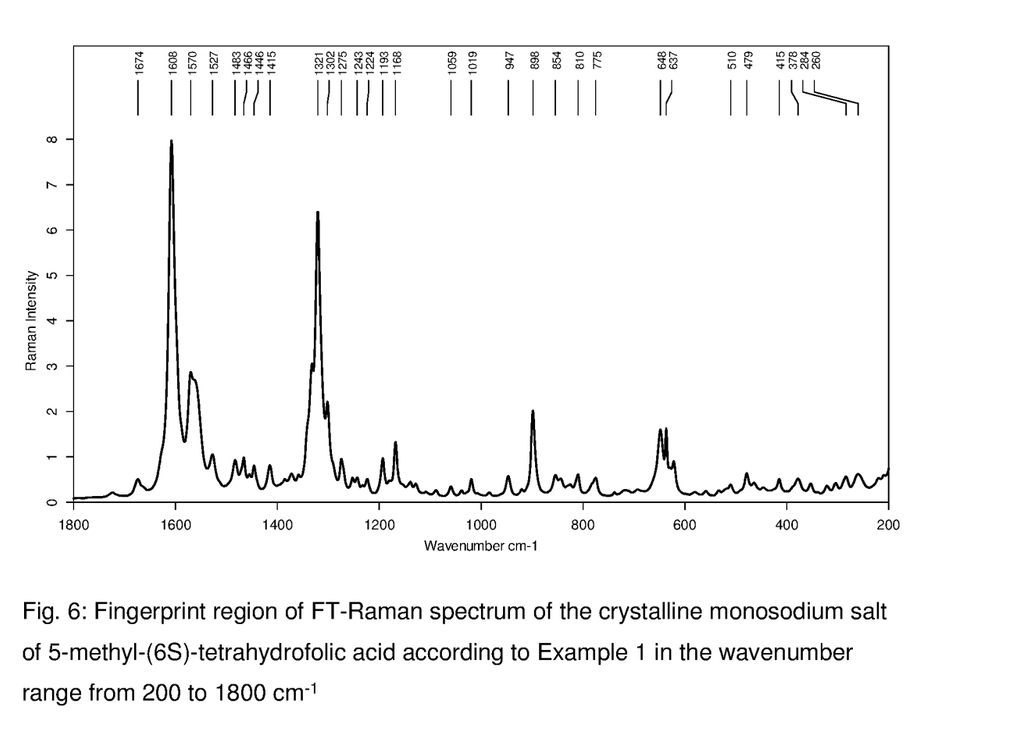
FIG. 6 shows the fingerprint region of FT-Raman spectrum of the crystalline monosodium salt of 5-methyl-(6S)-tetrahydrofolic acid according to Example 1 in the wavenumber range from 200 to 1800 cm$^{-1}$.

Yet a further aspect of the invention is the crystalline sodium salt of 5-methyl-(6S)-tetrahydrofolic acid which exhibits a Raman spectrum substantially as depicted in FIG. 6.

A further aspect of the present invention is a process for obtaining the crystalline sodium salt of 5-methyl-(6S)-tetrahydrofolic acid according to the present invention comprising the steps of:
a) providing of 5-methyl-(6S)-tetrahydrofolic acid, optionally in a suitable solvent or a mixture of solvents;
b) adding sodium hydroxide to the composition of step a);
c) optionally adding a solvent, a mixture of solvents and/or a co-salt former to the composition of step b), or adding the composition of step b) to a solvent, a mixture of solvents and/or a co-salt former;
d) crystallizing;
e) optionally adding more solvent or mixture of solvents; and
f) isolating the obtained solid.

Preferably, the molar ratio of 5-methyl-(6S)-tetrahydrofolic acid and sodium hydroxide in step b) is in the range of from 1:0.5 to 1:1.5 and even more preferred from 0.9 to 1.5.

In a further preferred embodiment, the molar ratio of 5-methyl-(6S)-tetrahydrofolic acid and the co-salt former in step c) is in the range of from 1:0.5 to 1:3, preferably in the range of from 1:0.9 to 1:2.5, even more preferred about 1:2.

Preferably, the solvent and/or mixtures of solvents according to step a), c) and/or e) is selected from the group consisting of water, water-soluble alcohols, methanol, ethanol, isopropanol, n-propanol, acetonitrile, tetrahydrofuran, acetone, methyl ethyl ketone, methyl isobutyl ketone, benzylalcohol, and mixtures thereof.

Preferably, the ratio of water to the solvent and/or mixtures of solvents in step d) and/or e) is 1:5 v/v or lower. More preferred is the ratio of water to the solvent and/or mixtures of solvents in step d) and/or e) 1:6 v/v or lower and even more preferred 1:7 v/v or lower. A higher water content in the solvent and/or mixtures of solvents in step d) and/or e) is resulting in lower crystallization yields.

A co-salt former as used herein is a chemical substance that facilitates the formation of the crystalline sodium salt according to the present invention. Co-salt formers according to the present invention are typically organic bases that are sufficiently soluble in the process solvents so that they are removed in the filtration step or can be easily washed off after filtration.

Preferably, the co-salt former in step c) is an organic base with a pKa value from 6 to 11 and even more preferred with a pKa value from 7 to 10.

In a further preferred embodiment, the co-salt former of step c) is selected from the group consisting of 4-(2-hydroxyethyl)-morpholine, 1-(2-hydroxyethyl)-pyrrolidine, imidazole, 2-dimethylaminoethanol, tert-butylamine, and mixtures thereof.

In a preferred embodiment, in step d) the temperature is at least 30° C., preferably at least 40° C., even more preferred at least 50° C., more preferred at least 60° C., further preferred at least 70° C. and most preferred at least 75° C.

Preferably, in step a), b), c) and/or d) seed crystals are added. Even more preferred the seed crystals are the desired sodium salt of 5-methyl-(6S)-tetrahydrofolic acid.

A further aspect of the present invention is a pharmaceutical composition, food additive, vitamin and/or other preparation comprising the crystalline sodium salt of 5-methyl-(6S)-tetrahydrofolic acid according to the present invention and optionally one or more acceptable excipients and the use of the crystalline sodium salt of 5-methyl-(6S)-tetrahydrofolic acid according to the present invention as constituent for the production of drugs and/or food additives.

The crystalline sodium salt of 5-methyl-(6S)-tetrahydrofolic acid of the present invention for use in homocysteine-lowering, the treatment of anemia, neural tube defects, cardiovascular diseases, depression, Alzheimer's disease, cognitive impairment and osteoporosis and/or dietary management of low plasma and/or low red blood cell folate and/or low cerebrospinal fluid folate and/or low peripheral or central nervous system folate is also part of the present invention.

Surprisingly, the crystalline sodium salt of 5-methyl-(6S)-tetrahydrofolic acid of the present invention has an improved kinetic solubility compared with the crystalline calcium salt disclosed in U.S. Pat. No. 6,441,168 B1. The measurement of the kinetic solubility was conducted as described in the experimental part.

The solubility of the crystalline sodium salt of 5-methyl-(6S)-tetrahydrofolic acid of the present invention in water (room temperature) is greater than 25 mg per 1 ml of water, whereas the calcium salt exhibits a solubility being considerably smaller than 10 mg per 1 ml of water.

Due to the higher solubility of the sodium salt of the present invention the bioavailability is better. This results in oral dosage forms, in which the amount of the active ingredient can be reduced, without diminishing the effectivity of the medicament or food additive.

Moreover, dynamic vapor sorption analysis (DVS) is a suitable method for investigating the hygroscopic properties and drying properties of a solid substance.

Figure 2:
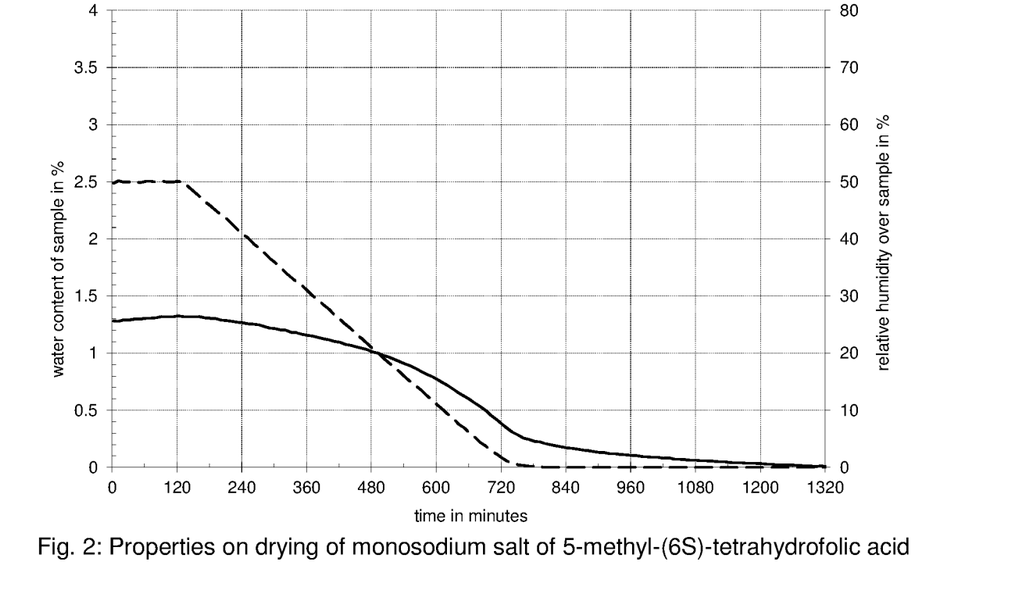
FIG. 2 shows the properties on drying of monosodium salt of 5-methyl-(6S)-tetrahydrofolic acid.

The crystalline sodium salt of 5-methyl-(6S)-tetrahydrofolic acid of the present invention can be dried sufficiently, so that after ten hours of nitrogen purge water can essentially be removed (Example 8, FIG. 2). Contrary thereto, the calcium salt of 5-methyl-(6S)-tetrahydrofolic acid still has a water content of 6 to 7% (Example 9, FIG. 3). The crystalline sodium salt of 5-methyl-(6S)-tetrahydrofolic acid of the present invention can be dried more easily.

Figure 4:
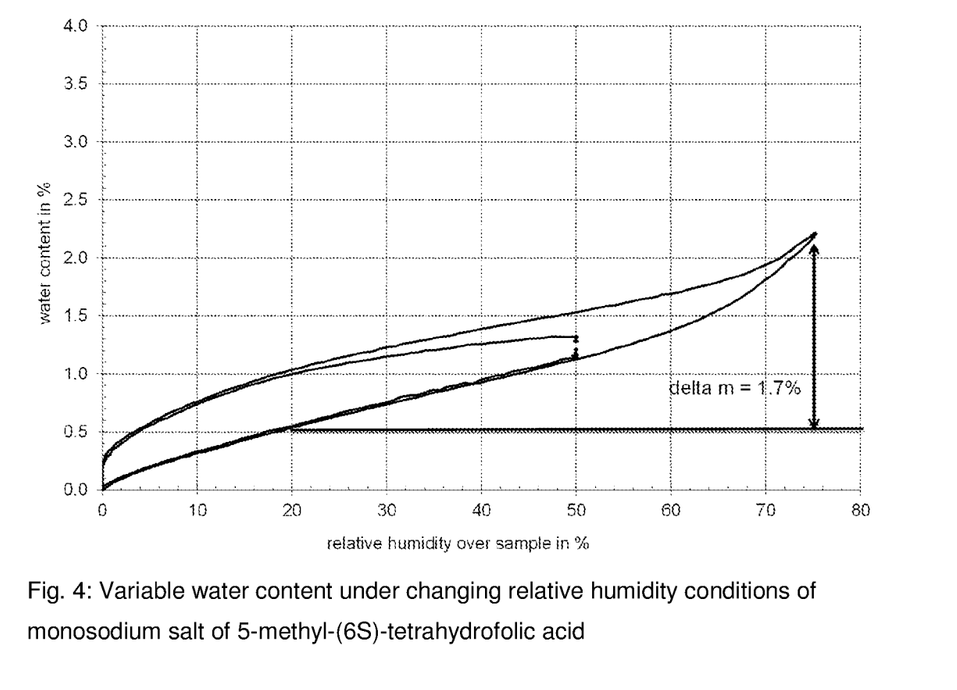
FIG. 4 shows the variable water content under changing relative humidity conditions of monosodium salt of 5-methyl-(6S)-tetrahydrofolic acid.

Moreover, the change of the water content within the most relevant range of relative humidity between 20% and 75% is about 1.7% for the crystalline sodium salt of 5-methyl-(6S)-tetrahydrofolic acid of the present invention (Example 10, FIG. 4). The calcium salt of 5-methyl-(6S)-tetrahydrofolic acid has a change of water content of about 3.5% (Example 11, FIG. 5). Thus, the crystalline sodium salt of 5-methyl-(6S)-tetrahydrofolic acid of the present invention is less hygroscopic which is desirable.

Additionally, the molecular weight of the sodium salt of 5-methyl-(6S)-tetrahydrofolic acid of the present invention is significant lower compared with the calcium salt of 5-methyltetrahydrofolic acid disclosed in U.S. Pat. No. 6,441,168 B1. A dosage form comprising the sodium salt of 5-methyl-(6S)-tetrahydrofolic acid of the present invention is having a lower weight compared with one comprising the calcium salt of 5-methyltetrahydrofolic acid containing an equivalent amount of the active substance. Thus, e.g. lighter and smaller tablets can be manufactured which is advantageous for patients like children, since said tablets can be swallowed more easily.

Pharmaceutical compositions according to the present invention can be applied for all modes of administration, preferably for oral, parenteral, intramuscular, intraspinal, intrathecal, peridontal, topical or rectal administration.

In summary, the profile of properties offered by the crystalline sodium salt of 5-methyl-(6S)-tetrahydrofolic acid of the present invention is advantageous for use in medicaments or as food additive.

In a $1^{st}$ aspect, a crystalline sodium salt of 5-methyl-(6S)-tetrahydrofolic acid wherein the molar ratio of 5-methyl-(6S)-tetrahydrofolic acid to sodium is from 1:0.5 to 1:1.5 and/or hydrates and/or solvates thereof.

In a $2^{nd}$ aspect, the crystalline salt of the $1^{st}$ aspect, wherein the molar ratio of 5-methyl-(6S)-tetrahydrofolic acid to sodium is from 1:0.75 to 1:1.25.

In a $3^{rd}$ aspect, the crystalline salt of the $1^{st}$ and $2^{nd}$ aspects, wherein the molar ratio of 5-methyl-(6S)-tetrahydrofolic acid to sodium is approximately 1:1.

In a $4^{th}$ aspect, the crystalline salt of at least one of the preceding aspects, characterized in that the salt is the sodium salt of 5-methyl-(6S)-tetrahydrofolic acid and has a PXRD pattern with at least one characteristic peak (expressed in 2θ±0.2° 2θ (CuKα radiation)) at 6.5, 10.2, 13.1, 15.3, 17.9, 20.5, and 22.0.

In a $5^{nd}$ aspect, the crystalline salt of at least one of the preceding aspects, characterized in that the salt is the sodium salt of 5-methyl-(6S)-tetrahydrofolic acid and has a PXRD pattern with at least one characteristic peak (expressed in 2θ±0.2° 2θ (CuKα radiation)) at 6.5, 10.2, 12.5, 13.1, 14.8, 15.1, 15.3, 16.1, 17.2, 17.9, 20.4, 20.5, 21.2, 22.0, 22.5, and 27.2.

In a $6^{th}$ aspect, the crystalline salt of at least one of the preceding aspects, characterized in that the sodium salt of 5-methyl-(6S)-tetrahydrofolic acid has a PXRD pattern substantially as shown in FIG. 1.

In a $7^{th}$ aspect, the crystalline salt of at least one of the preceding aspects, characterized in that the sodium salt of 5-methyl-(6S)-tetrahydrofolic acid is a monosodium salt of 5-methyl-(6S)-tetrahydrofolic acid.

In an $8^{th}$ aspect, the crystalline salt of at least one of the preceding aspects having at least 99% or more chemical and stereoisomerical purity.

In a $9^{th}$ aspect, a process for obtaining the crystalline sodium salt of 5-methyl-(6S)-tetrahydrofolic acid according to at least one of the $1^{st}$ to $7^{th}$ aspects comprising the steps of:

a) providing of 5-methyl-(6S)-tetrahydrofolic acid, optionally in a suitable solvent or a mixture of solvents;
b) adding sodium hydroxide to the composition of step a);
c) optionally adding a solvent, a mixture of solvents and/or a co-salt former to the composition of step b), or adding the composition of step b) to a solvent, a mixture of solvents and/or a co-salt former;
d) crystallizing;
e) optionally adding more solvent or mixture of solvents; and
f) isolating the obtained solid.

In a $10^{th}$ aspect, the process of the $9^{th}$ aspect, characterized in that the molar ratio of 5-methyl-(6S)-tetrahydrofolic acid and sodium hydroxide in step b) is in the range of from 1:0.5 to 1:1.5.

In an $11^{th}$ aspect, the process of the $9^{th}$ or $10^{th}$ aspects, characterized in that the molar ratio of 5-methyl-(6S)-tetrahydrofolic acid and the co-salt former in step c) is in the range of from 1:0.5 to 1:3.

In a $12^{th}$ aspect, the process of at least one of the $9^{th}$ to $11^{th}$ aspects, characterized in that solvent and/or mixtures of solvents according to step a), c) and/or e) is selected from the group consisting of water, water-soluble alcohols, methanol, ethanol, isopropanol, n-propanol, acetonitrile, tetrahydrofuran, acetone, methyl ethyl ketone, methyl isobutyl ketone, benzylalcohol, and mixtures thereof.

In a $13^{th}$ aspect, the process of at least one of the $9^{th}$ to $12^{th}$ aspects, characterized in that the co-salt former of step c) is an organic base with a pKa value from 6 to 11.

In a $14^{th}$ aspect, the process of at least one of the $9^{th}$ to $13^{th}$ aspects, characterized in that the co-salt former of step c) is an organic base with a pKa value from 7 to 10.

In a $15^{th}$ aspect, the process of at least one of the $9^{th}$ to $14^{th}$ aspects, characterized in that a co-salt former of step c) is selected from the group consisting of 4-(2-hydroxyethyl)-morpholine, 1-(2-hydroxyethyl)-pyrrolidine, imidazole, 2-dimethylaminoethanol, and tert-butylamine; and mixtures thereof.

In a $16^{th}$ aspect, the process of the $15^{th}$ aspect, characterized in that a co-salt former of step c) is 4-(2-hydroxyethyl)-morpholine.

In a $17^{th}$ aspect, the process of at least one of the $9^{th}$ to $16^{th}$ aspects, characterized in that in step d) the temperature is at least 30° C.

In an $18^{th}$ aspect, the process of at least one of the $9^{th}$ to $17^{th}$ aspects, characterized in that in step a), b), c) and/or d) seed crystals are added.

In a $19^{th}$ aspect, a pharmaceutical composition, food additive, vitamin and/or other preparation comprising the crystalline sodium salt of 5-methyl-(6S)-tetrahydrofolic acid according to at least one of the $1^{st}$ to $7^{th}$ aspects and optionally one or more acceptable excipients.

In a $20^{th}$ aspect, the pharmaceutical composition according to the $19^{th}$ aspect in the form of tablets, capsules, oral liquid preparations, powders, lyophilisates, granules, lozenges, reconstitutable powders, injectable or infusable solutions or suspensions or suppositories.

In a $21^{th}$ aspect, the pharmaceutical composition according to the $19^{th}$ to $20^{th}$ aspects further comprising at least one additional therapeutic agent.

In a $22^{nd}$ aspect, the pharmaceutical composition according to the $19^{th}$ to $21^{st}$ aspects, which is a pharmaceutical composition for oral, parenteral, intramuscular, intraspinal, intrathecal, peridontal, topical or rectal administration.

In a 23rd aspect, the use of the crystalline sodium salt of 5-methyl-(6S)-tetrahydrofolic acid according to at least one of the 1st to 7th aspects as constituent for the production of drugs and/or food additives.

In a 24th aspect, the crystalline sodium salt of 5-methyl-(6S)-tetrahydrofolic acid according to at least one of the 1st to 7th aspects for use in the treatment in homocysteine-lowering, of anemia, neural tube defects, cardiovascular diseases, depression, cognitive impairment, Alzheimer's disease and osteoporosis and/or dietary management of low plasma and/or low red blood cell folate and/or low cerebrospinal fluid folate and/or low peripheral or central nervous system folate.

EXPERIMENTAL

Powder X-Ray Diffraction

Stoe Stadi P equipped with a Mythen1 K Detector; Cu-Kα1 radiation; standard measurement conditions: transmission; 40 kV and 40 mA tube power; curved Ge monochromator; 0.02°2θ step size, 48 s step time, 1.5-50.5°2θ scanning range; detector mode: step scan; 1°2θ detector step; standard sample preparation: 10 to 20 mg sample was placed between two acetate foils; sample holder: Stoe transmission sample holder; the sample was rotated during the measurement. All sample preparation and measurement was done in an ambient air atmosphere.

TG-FTIR

Thermogravimetric measurements were carried out with a Netzsch Thermo-Microbalance TG 209 coupled to a Bruker FTIR Spectrometer Vector 22 (sample pans with a pinhole, $N_2$ atmosphere, heating rate 10 K/min).

DVS

DVS measurements are typically performed at 25° C. with an SPS11-100n "Sorptions Prüfsystem" from ProUmid (formerly "Projekt Messtechnik"), August-Nagel-Str. 23, 89079 Ulm (Germany). About 20 mg of sample are placed put into an aluminum sample pan. Humidity change rates of 5% per hour were used. The applied measurement program is visualized in the figure (dashed trace) and described below.

The sample was placed on an aluminum holder on top of a microbalance and allowed to equilibrate at 50% RH before starting the pre-defined humidity program in the following way:

(1) 2 hours at 50% relative humidity
(2) 50→0% relative humidity (5%/hour); 10 hours at 0% relative humidity
(3) 0→75% relative humidity (5%/hour); 5 hours at 75% relative humidity
(4) 75→0% relative humidity (5%/hour); 10 hours at 0% relative humidity
(5) 0→50% relative humidity (5%/hours); 2 hours at 50% relative humidity Raman Spectroscopy:

FT-Raman spectra were recorded on a Bruker MultiRAM FT-Raman or a Bruker RFS 100 FT-Raman system with a near infrared Nd:YAG laser operating at 1064 nm and a liquid nitrogen-cooled germanium detector. 64 scans with a resolution of 2 $cm^{-1}$ were accumulated in the range from 3500 to −50 $cm^{-1}$; however, only data above 100 $cm^{-1}$ are evaluated due to filter cutoff effects. Nominal laser powers are typically 100 or 300 mW.

Example 1: Preparation of Crystalline Monosodium Salt of 5-methyl-(6S)-tetrahydrofolic Acid with Imidazole as Co-Salt Former without Seeding To 467 mg of 5-methyl-(6S)-tetrahydrofolic acid monohydrate (assay 5-methyltetrahydrofolic acid 97.65% w/w) were weighed into a glass vial equipped with a magnetic stirrer bar. 1.0 mL of sodium hydroxide standard solution 1.00 mol/L and 76 mg of imidazole were added. At ambient temperature, an essentially clear solution was obtained to which 7.0 mL of ethanol was added. The addition of ethanol led to a thick suspension at room temperature. The suspension was heated to 80° C. and stirred for two hours before the solid was separated by hot filtration using a fritted glass filter (porosity P4) and dried in air at room temperature. The filter cake was washed with 10 mL ethanol and let dry in air for about 30 minutes. 320 mg (63% yield, assay 5-methyltetrahydrofolic acid 89.38% w/w) of a fine, slightly yellow powder was obtained as the product and was characterized by powder X-ray diffraction (FIG. 1, Table 1) and Raman spectroscopy (FIG. 6, Table 2). The sodium content found by ICP-OES was 4.49% which is in good agreement with a monosodium salt. HPLC analysis showed a purity of 97.4 in area-% and thus confirmed the identity of the salt.

TABLE 1

Powder X-ray diffraction data for crystalline monosodium salt of Example 1 with 2-theta angles, d-spacing values in Ångstrom and qualitative intensity values as follows: vs = very strong, s = strong, m = medium, w = weak and vw = very weak.

| °2-theta | d-spacings [Å] | intensity (qualitative) |
|---|---|---|
| 6.5 | 13.5 | m |
| 10.2 | 8.6 | vs |
| 12.5 | 7.1 | vw |
| 13.1 | 6.8 | s |
| 14.8 | 5.99 | s |
| 15.1 | 5.87 | s |
| 15.3 | 5.79 | vs |
| 15.8 | 5.61 | w |
| 16.1 | 5.50 | s |
| 17.2 | 5.15 | s |
| 17.9 | 4.94 | vs |
| 19.7 | 4.51 | vw |
| 20.0 | 4.44 | w |
| 20.4 | 4.35 | s |
| 20.5 | 4.32 | vs |
| 21.0 | 4.22 | w |
| 21.2 | 4.18 | s |
| 21.5 | 4.13 | w |
| 22.0 | 4.03 | vs |
| 22.5 | 3.95 | vs |
| 24.7 | 3.61 | w |
| 25.3 | 3.51 | m |
| 25.5 | 3.48 | w |
| 25.9 | 3.44 | w |
| 26.4 | 3.38 | w |
| 26.9 | 3.31 | m |
| 27.2 | 3.27 | s |
| 27.6 | 3.23 | w |
| 27.9 | 3.20 | w |
| 28.4 | 3.14 | m |
| 28.6 | 3.12 | m |
| 28.8 | 3.09 | vw |
| 29.3 | 3.04 | vw |
| 29.7 | 3.01 | m |
| 30.2 | 2.96 | w |
| 30.4 | 2.94 | vw |
| 30.9 | 2.89 | w |
| 31.2 | 2.86 | w |
| 31.9 | 2.81 | m |

TABLE 2

Raman data for the crystalline monosodium salt of Example 1 with wavenumber in cm$^{-1}$ and intensity values. It should be noted that the intensities vary with Laser power, sample amount and other factors.

| wavenumber (cm$^{-1}$) | intensity (arbitrary units) |
|---|---|
| 3079 | 0.43 |
| 3036 | 0.49 |
| 2991 | 0.51 |
| 2962 | 0.82 |
| 2941 | 1.20 |
| 2927 | 0.90 |
| 2902 | 0.87 |
| 2852 | 0.62 |
| 1674 | 0.51 |
| 1608 | 7.98 |
| 1570 | 2.87 |
| 1527 | 1.06 |
| 1483 | 0.93 |
| 1466 | 0.99 |
| 1446 | 0.80 |
| 1415 | 0.81 |
| 1321 | 6.43 |
| 1302 | 2.22 |
| 1274 | 0.96 |
| 1243 | 0.55 |
| 1224 | 0.51 |
| 1193 | 0.97 |
| 1168 | 1.33 |
| 1059 | 0.35 |
| 1019 | 0.51 |
| 947 | 0.57 |
| 898 | 2.03 |
| 854 | 0.60 |
| 810 | 0.61 |
| 775 | 0.54 |
| 648 | 1.60 |
| 637 | 1.62 |
| 510 | 0.39 |
| 479 | 0.64 |
| 415 | 0.51 |
| 378 | 0.52 |
| 284 | 0.57 |
| 260 | 0.62 |
| 196 | 0.83 |

Example 2: Preparation of the Crystalline Monosodium Salt of 5-methyl-(6S)-tetrahydrofolic Acid in Isopropanol with 4-(2-hydroxyethyl)-morpholine as Co-Salt Former and Seeding To 467 mg of 5-methyl-(6S)-tetrahydrofolic acid monohydrate (assay 5-methyltetrahydrofolic acid 97.65% w/w) were weighed into a glass vial equipped with a magnetic stirrer bar. 1.0 mL of sodium hydroxide standard solution 1.00 mol/L and 140 μl of 4-(2-hydroxyethyl)-morpholine were added. At ambient temperature, an essentially clear solution was obtained to which 7.0 mL of isopropanol was added. The addition of isopropanol led to a thick suspension at room temperature. The suspension was heated to 80° C. and stirred for one hour then seed crystals of 5-methyl-(6S)-tetrahydrofolic acid monosodium salt according to example 1 were added and stirring at 80° C. was continued for one hour before the solid was separated by hot filtration using a fritted glass filter (porosity P4) and dried in air at room temperature. The filter cake was washed with 10 mL isopropanol and let dry in air at r.t. for about 30 minutes. 413 mg of a fine, slightly yellow powder was obtained as the product. Powder X-ray diffraction confirmed the identity of the monosodium salt.

Example 3: Preparation of the Crystalline Monosodium Salt of 5-methyl-(6S)-tetrahydrofolic acid with 4-(2-hydroxyethyl)-morpholine as Co-Salt Former and Seeding 4.694 g of 5-methyl-(6S)-tetrahydrofolic acid monohydrate (assay 5-methyltetrahydrofolic acid 97.65% w/w) were weighed into a 100 mL glass flask equipped with a magnetic stirrer bar. 10.00 mL of sodium hydroxide standard solution 1.00 mol/L and 1.470 mL of 4-(2-hydroxyethyl)-morpholine were added. After stirring at room temperature for 10 minutes a brown clear solution was formed. While stirring the solution at room temperature, 50 mL ethanol was added. A turbid solution was present after stirring for 6 minutes. The mixture was seeded with 56 mg of crystalline MTHF monosodium salt according to example 1 and after stirring for 5 minutes at room temperature a thick suspension formed, which was no longer stirrable using a magnetic stirrer bar. Thus the mixture was heated to 80° C. within about 6 minutes and a light brown suspension was formed which was easy to stir. The sample was seeded again with 36 mg of crystalline MTHF mono-Na salt. After stirring for 6 minutes at 80° C. a yellow suspension was present with some off-white solid material that adhered to the glass wall. After stirring the suspension at 80° C. for 75 minutes 20 mL of ethanol were added to the yellow suspension and stirring was continued for 70 minutes before the solid product was filtered off by hot filtration using a fritted glass filter (porosity P4, Ø 5 cm) and the filter cake was air dried for about 2 minutes. 16 mL of an ethanol-water mixture 7:1 (v/v) was added to the filter cake and the washing solution was pulled through the filter by vacuum suction. The wash step was repeated with another 16 mL of the same ethanol-water mixture. The filter cake was then air dried for 20 minutes (air was drawn through the fritted glass filter; 24° C., 41% relative humidity). After about 10 minutes the filter cake was broken into smaller pieces and lumps were slightly crushed using a spatula. After 20 minutes the solid material was transferred into a 40 mL glass bottle. 4.36 grams (about 86% yield, assay 5-methyltetrahydrofolic acid 89.94% w/w) of a fine, slightly yellow powder was obtained as the solid product and was characterized by powder X-ray diffraction, H-NMR spectroscopy and TG-FTIR. Light microscopy and PXRD confirmed the crystalline nature of the sample and H-NMR spectroscopy was in agreement with the chemical integrity of 5-methyl-(6S)-tetrahydrofolic acid and showed no significant amount of 4-(2-hydroxyethyl)-morpholine. Further investigation by TG-FTIR revealed a mass loss of about 1.6%, attributable to water. The sodium content found by ICP-OES was 4.59% which is in good agreement with a monosodium salt. HPLC showed a purity of 97.4%.

Example 4: Preparation of the Crystalline Monosodium Salt of 5-methyl-(6S)-tetrahydrofolic Acid with 4-(2-hydroxyethyl)-morpholine as Co-Salt Former and Seeding The first step of the experiment was carried out in a separate vial in order to prevent seeds of crystalline MTHF free acid in the larger glass reactor. 9.3888 grams of 5-methyl-(6S)-tetrahydrofolic acid monohydrate (assay 5-methyltetrahydrofolic acid 97.65% w/w) were weighed into a 60 mL glass vessel equipped with a magnetic stirrer bar. 20.00 mL of sodium hydroxide standard solution 1.00 mol/L and 2.940 mL of 4-(2-hydroxyethyl)-morpholine were added. After stirring at room temperature for about 15 minutes a brown clear solution was formed with pH of about 6.9. This solution was transferred into a 350 mL glass reactor and stirred with a paddle stirrer. The gas phase was purged using a dry nitrogen flow and the mixture heated to 80° C. within about 20 minutes. At 80° C. a solution was still present and 20 mL of ethanol were added within about 6 minutes before 7 mg of crystalline MTHF monosodium salt according to example 1 was added as seed crystals. Within about 13 minutes an additional 50 mL of ethanol were added while stirring (about 340 rpm). During the addition of ethanol the solution was seeded several times using 5 mg to 7 mg of the same seed crystals but a turbid solution rather than a suspension was observed. Within about 85 minutes an additional 80 mL of ethanol (in total 150 mL) were added while stirring. During the addition of ethanol the seeding was performed several times each time using 3 mg to 9 mg of the same seeding crystals. However by visual observation, the system was judged as an emulsion with slightly brown material adhering to the glass wall of the reactor. The mixture was then stirred at 80° C. for 10 minutes and a small amount of the light brown material was scraped from the glass wall using a spatula. Over time, a weak suspension formed. While stirring some material that adhered to the glass wall was redispersed by scraping it from the glass wall using a spatula. After stirring at 500 rpm at 80° C. for about 2.5 hours a yellow suspension had formed that was easy to stir but still contained relatively small brown lumps. Hot filtration was carried out using a fritted glass filter (porosity P4, Ø5 cm) and the filter cake was air dried for about 2 minutes. The glass reactor was washed twice with 30 mL of an ethanol-water mixture 7:1 (v/v) that was added to the filter cake and the wash solution was pulled through the filter by vacuum suction. The filter cake was then washed a third time using 30 mL using the same ethanol-water mixture. The filter cake was then air dried for 30 minutes (air was drawn through the fritted glass filter; 23° C., 59% relative humidity). After about 7 minutes the filter cake was broken into smaller pieces and lumps were slightly crushed using a spatula. After 30 minutes the solid product (8.28 grams) was transferred into a 60 mL glass container and a sample was drawn for analysis by PXRD, which confirmed the presence of crystalline MTHF mono-Na salt. The remaining solid material was vacuum dried at 80° C./about 10 mbar for 0.5 hour. The solid product was 8.05 g (yield about 78%, assay 5-methyltetrahydrofolic acid 89.12% w/w) of a fine, slightly yellow powder. Characterization by PXRD showed that drying did not lead to a change of the crystalline form. H-NMR spectroscopy confirmed the chemical integrity of 5-methyl-(6S)-tetrahydrofolic acid and showed no significant amount of 4-(2-hydroxyethyl)-morpholine. The sample was further investigated by TG-FTIR and HPLC. HPLC showed a purity of 96.5%.

Example 5: Preparation of the Crystalline Monosodium Salt of 5-methyl-(6S)-tetrahydrofolic Acid in Ethanol with 2-diethylaminoethanol as Co-Salt Former and Seeding To 467 mg of 5-methyl-(6S)-tetrahydrofolic acid monohydrate (assay 5-methyltetrahydrofolic acid 97.65% w/w) were weighed into a glass vial equipped with a magnetic stirrer bar. 1.0 mL of sodium hydroxide standard solution 1.00 M, 5.0 mL ethanol and 100 µl of 2-diethylaminoethanol were added. The mixture was heated to 80° C. under stirring and then seed crystals of 5-methyl-(6S)-tetrahydrofolic acid monosodium salt according to example 1 were added and stirring at 80° C. was continued for one hour before the solid was separated by hot filtration using a fritted glass filter (porosity P4) and dried in air at room temperature. 370 mg (55% yield, assay 5-methyltetrahydrofolic acid 68.2% w/w) of solid product was obtained and characterized by powder X-ray diffraction and HPLC. HPLC showed a purity of 93.7%.

Example 6: Kinetic Solubility of the Crystalline Monosodium Salt of 5-methyl-(6S)-tetrahydrofolic Acid Step 1: 23.8 mg of crystalline 5-methyl-(6S)-tetrahydrofolic acid monosodium salt are weighed into a 7 ml glass vial with screw cap. 2.38 ml of purified/de-ionized water (for instance water for chromatography) is added to the solid using an adjustable volumetric pipette. The mixture is vigorously agitated at room temperature and briefly sonicated and a clear slightly yellow solution is readily obtained. Thus the solubility is greater than 10 mg per 1 ml of water. The solution remains clear for more than 20 hours at r.t.

Step 2: 62.3 mg of crystalline monosodium salt are weighed into a 7 ml glass vial with screw cap. 4.15 ml of purified/de-ionized water (for instance water for chromatography) is added to the solid using an adjustable volumetric pipette. The mixture is vigorously agitated at room temperature and briefly sonicated and a clear slightly yellow solution is readily obtained. Thus the solubility is greater than 15 mg per 1 ml of water. The solution remains clear for several hours at r.t.

Step 3: 72.6 mg of crystalline MTHF monosodium salt are weighed into a 7 ml glass vial with screw cap. 2.9 ml of purified/de-ionized water (for instance water for chromatography) is added to the solid using an adjustable volumetric pipette. The mixture is vigorously agitated at room temperature and briefly sonicated and a clear slightly yellow solution is readily obtained. Thus the solubility is greater than 25 mg per 1 ml of water. The solution remains clear for about one hour at r.t.

Reference Example 7: Kinetic Solubility of the Calcium Salt of 5-methyl-(6S)-tetrahydrofolic Acid 27.9 mg of crystalline calcium salt of MTHF (containing about 11% of water, thus corresponding to a dry weight of about 25 mg) are weighed into a 4 ml glass vial with screw cap. 2.535 ml of purified/de-ionized water (for instance water for chromatography) is added to the solid using an adjustable volumetric pipette. The mixture is vigorously agitated at room temperature and briefly sonicated. No clear solution can be obtained and a fairly concentrated suspension persists; thus the solubility is considerable smaller than 10 mg per 1 ml of water.

Example 8: Properties on Drying of the Crystalline Monosodium Salt of 5-methyl-(6S)-tetrahydrofolic Acid A sample of crystalline monosodium salt according to at least one of the previous examples is investigated by thermogravimetry coupled with infrared spectroscopy (TG-FTIR). Thermogravimetric measurements were done with a sample mass of about 6 mg. The mass loss at 200° C. is about 1.3% which essentially corresponds to the water content of the crystalline monosodium salt after drying in air at room temperature. The same sample is now examined by dynamic vapor sorption analysis (DVS). About 20 mg of sample are placed put into an aluminum sample pan. Humidity change rates of 5% per hour were used. The applied measurement program is visualized in the figure (dashed trace) and described below. The presentation shows the effective water content with a correction based upon TG-FTIR result. The sample was placed on an aluminum holder on top of a microbalance and allowed to equilibrate at 50% RH before starting the pre-defined humidity program in the following way:
(1) 2 hours at 50% relative humidity
(2) 50→0% relative humidity (5%/hour); 10 hours at 0% relative humidity
(3) 0→75% relative humidity (5%/hour); 5 hours at 75% relative humidity
(4) 75→0% relative humidity (5%/hour); 10 hours at 0% relative humidity
(5) 0→50% relative humidity (5%/hour); 2 hours at 50% relative humidity The result as shown in the FIG. 2 shows that all the water of the sample is essentially removed after ten hours of nitrogen purge at room temperature.

Figure 3:
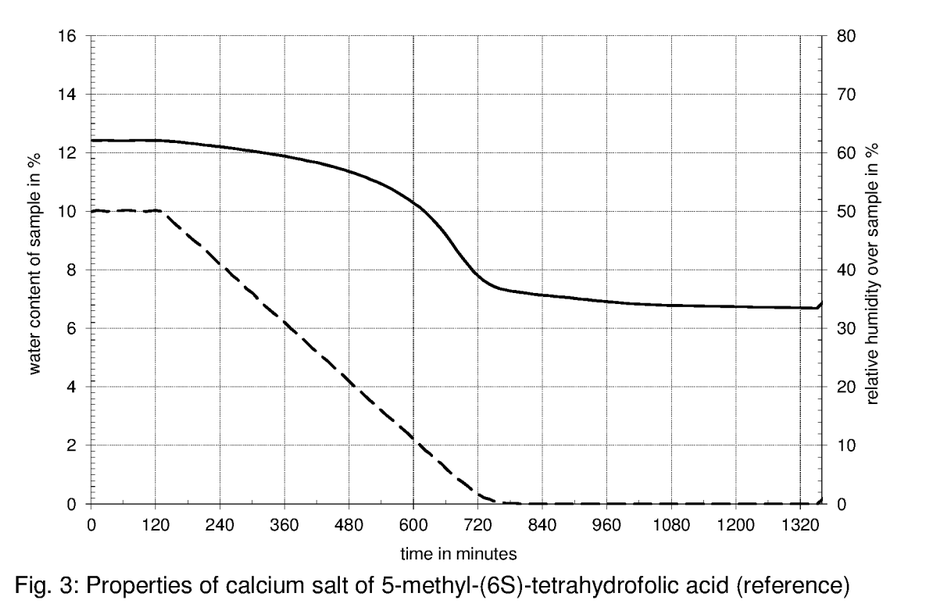
FIG. 3 shows the properties of calcium salt of 5-methyl-(6S)-tetrahydrofolic acid, as a reference.

Reference Example 9: Drying of the Calcium Salt of 5-methyl-(6S)-tetrahydrofolic Acid A sample of crystalline calcium salt of MTHF is examined by Karl Fischer titration to evaluate the water content. The water content found is 12.4%. Thereafter the same sample is investigated by DVS according to the very same measurement program as for the monosodium salt of the example above. The results as shown in FIG. 3 that after 10 hours of drying under nitrogen at room temperature the water content is still on the order of 6 to 7% which means that less than half of the water can be removed under identical conditions.

Example 10: Water Content of the Crystalline Monosodium Salt of 5-methyl-(6S)-tetrahydrofolic Acid Under Changing Relative Humidity Conditions A sample of crystalline monosodium salt of MTHF according to at least one of the previous examples is investigated by thermogravimetry coupled with infrared spectroscopy (TG-FTIR). Thermogravimetric measurements were done with a sample mass of about 6 mg. The mass loss at 200° C. is about 1.3% which essentially corresponds to the water content of the crystalline monosodium salt after drying in air at room temperature. The same sample is now examined by dynamic vapor sorption analysis (DVS). About 20 mg of sample are placed put into an aluminum sample pan. Humidity change rates of 5% per hour were used. Where applicable, the applied measurement program is visualized in the figure (dashed trace) and described below. The presentation shows the effective water content with a correction based upon TG-FTIR result. The sample was placed on an aluminum or platinum holder on top of a microbalance and allowed to equilibrate at 50% RH before starting the pre-defined humidity program in the following way:
(1) 2 hours at 50% relative humidity
(2) 50→0% relative humidity (5%/hour); 10 hours at 0% relative humidity
(3) 0→75% relative humidity (5%/hour); 5 hours at 75% relative humidity
(4) 75→0% relative humidity (5%/hour); 10 hours at 0% relative humidity
(5) 0→50% relative humidity (5%/hour); 2 hours at 50% relative humidity The result as shown in the FIG. 4 shows that the change of the water content within the most relevant range of relative humidity between 20% and 75% is about 1.7%.

Figure 5:
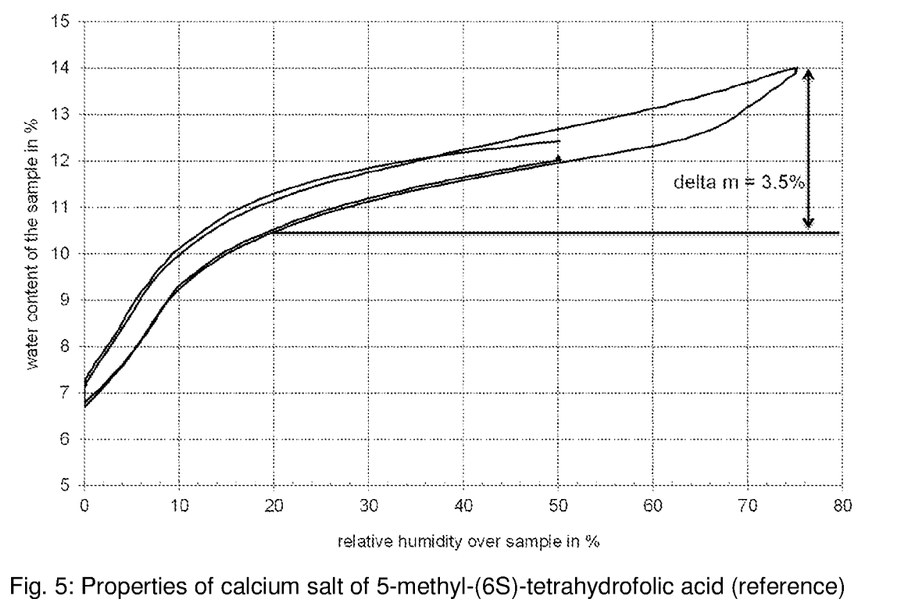
FIG. 5 shows the properties of calcium salt of 5-methyl-(6S)-tetrahydrofolic acid, as a reference.

Reference Example 11: Water Content of the Calcium Salt of 5-methyl-(6S)-tetrahydrofolic Acid Under Changing Relative Humidity Conditions A sample of crystalline calcium salt of MTHF is subjected to the very same relative humidity program in a DVS instrument. The results as depicted in FIG. 5 shows that the change of the water content within the most relevant range of relative humidity between 20% and 75% is about 3.5%.

Example 12: Preparation of the Crystalline Monosodium Salt of 5-methyl-(6S)-tetrahydrofolic Acid with 2 Equivalents of 4-(2-hydroxyethyl)-morpholine as Co-Salt Former To a mixture of 40 g 5-methyl-(6S)-tetrahydrofolic acid (assay 5-methyltetrahydrofolic acid 95.4% w/w) and 86 g water, 3.46 g solid sodium hydroxide and 21.79 g 4-(2-hydroxyethyl) morpholine were added at room temperature under a nitrogen atmosphere while stirring. The mixture was added within 5.5 hours to a mixture of 472 g ethanol with 5% v/v 2-propanol and 0.4 g crystalline monosodium salt of 5-methyl-(6S)-tetrahydrofolic acid at 75-78° C. under a nitrogen atmosphere while stirring. 3 g water were added and the mixture was stirred for an additional hour at 76° C. The solids were separated by filtration, washed three times with each 133 mL ethanol 5% 2-propanol/water 7:1 v/v and dried in vacuum at 40° C. for 16.5 hours to give 42.0 g of an off-white powder corresponding to 102% yield (assay 5-methyltetrahydrofolic acid 92.45% w/w). PXRD confirmed the crystalline nature of the sample and H-NMR spectroscopy was in agreement with the chemical integrity of 5-methyl-(6S)-tetrahydrofolic acid and showed no significant amount of 4-(2-hydroxyethyl)-morpholine. Further investigation by TGA (Thermogravimetric Analysis) revealed a mass loss of about 0.86%. The sodium content found by IC (Ion chromatography) was 4.94% which is in good agreement with a monosodium salt. HPLC showed a purity of 98.2%.

Example 13: Preparation of the Crystalline Monosodium Salt of 5-methyl-(6S)-Tetrahydrofolic Acid with a Purity of 98.6% by Recrystallization of Crystalline Monosodium Salt of 5-methyl-(6S)-tetrahydrofolic Acid in the Presence of 1 Equivalent of 4-(2-hydroxyethyl)-morpholine 2 g crystalline monosodium salt of 5-methyl-(6S)-tetrahydrofolic acid (assay 5-methyltetrahydrofolic acid 92.63% w/w) were added to a mixture of 10 g water and 0.51 g 4-(2-hydroxyethyl) morpholine under a nitrogen atmosphere. After stirring for 10 minutes at 25° C., the mixture was added to a mixture of 70 mL ethanol with 5% v/v 2-propanol and 0.05 g crystalline monosodium salt of 5-methyl-(6S)-tetrahydrofolic acid at 72° C. within 2.5 hours under a nitrogen atmosphere while stirring. The mixture was stirred for additional 2.5 hours at 72° C. The solids were separated by filtration, washed with 20 mL ethanol 5% 2-propanol/water 7:1 v/v and dried in vacuum at 33° C. for 18 hours to give 1.75 g of an off-white powder corresponding to 87% yield (assay 5-methyltetrahydrofolic acid 92.5% w/w). PXRD confirmed the crystalline nature of the sample and H-NMR spectroscopy was in agreement with the chemical integrity of 5-methyl-(6S)-tetrahydrofolic acid and showed no significant amount of 4-(2-hydroxyethyl)-morpholine. Further investigation by TGA (Thermogravimetric Analysis) revealed a mass loss of about 1.48%. The sodium content found by IC (Ion chromatography) was 4.83% which is in good agreement with a monosodium salt. HPLC showed a purity of 98.6%.

Example 14: Preparation of the Crystalline Monosodium Salt of 5-methyl-(6S)-tetrahydrofolic Acid Starting from a Crystalline 1:1:1 Salt of 5-methyl-(6S)-tetrahydrofolic Acid, Sodium and 4-(2-hydroxyethyl)-morpholine 5 g of a 1:1:1 salt of 5-methyl-(6S)-tetrahydrofolic acid, sodium and 4-(2-hydroxyethyl)-morpholine (assay 5-methyltetrahydrofolic acid 70.60% w/w) were suspended in a mixture of 49.4 g ethanol 5% v/v 2-propanol and 12.5 g water under a nitrogen atmosphere. The mixture was stirred for 3 hours at 74° C. The solids were separated by filtration and washed with 17 mL of a mixture of ethanol/water 7:1 v/v. The solids were dried at 40° C. in vacuum to give 2.93 g of an off-white powder corresponding to 78% yield (assay 5-methyltetrahydrofolic acid 93.65% w/w). PXRD confirmed the crystalline nature of the sample and H-NMR spectroscopy was in agreement with the chemical integrity of 5-methyl-(6S)-tetrahydrofolic acid and showed no significant amount of 4-(2-hydroxyethyl)-morpholine. Further investigation by TGA (Thermogravimetric Analysis) revealed a mass loss of about 0.30%. The sodium content found by IC (Ion chromatography) was 4.56% which is in good agreement with a monosodium salt. HPLC showed a purity of 99.02%.

Example 15: Preparation of the Crystalline Monosodium Salt of 5-methyl-(6S)-tetrahydrofolic Acid in Larger Scale All operations were performed under a nitrogen atmosphere if nothing else is mentioned. Solvents in the reaction and crystallization vessel were condensed during heating.

9.6 kg of 4-(2-hydroxyethyl) morpholine were added to 101.7 kg of a mixture of water/ethanol (5% 2-propanol) 1:1 v/v in a reaction vessel at room temperature while stirring. Further 1.0 kg of water/ethanol (5% 2-propanol) 1:1 v/v were added followed by 28.8 kg 5-methyl-(6S)-tetrahydrofolic acid (assay 5-methyltetrahydrofolic acid 97.17% w/w) while stirring. Additional 2 kg of a mixture of water/ethanol (5% 2-propanol) 1:1 v/v were added. Then 8.7 kg of an aqueous solution of sodium hydroxide were added (assay sodium hydroxide 29.22% w/w) to the reaction vessel followed by 1 kg of a mixture of water/ethanol (5% 2-propanol) 1:1 v/v. The mixture was heated to 38° C. and the pH of the resulting solution was 7.56. The solution was transferred from the reaction vessel over a filter into a crystallization vessel. The transfer pipes and the filter were washed with 9.8 kg of a mixture of water/ethanol (5% 2-propanol) 1:1 v/v. The washings were added to the filtrate. The filtrate was heated to 75.1° C. while stirring and within 59 minutes 53.8 kg ethanol (5% 2-propanol) were added while maintaining the temperature between 75.1 and 80.4° C. The mixture was cooled to 64.8° C. and 0.29 kg of crystalline monosodium salt of 5-methyl-(6S)-tetrahydrofolic acid were added for seeding. The mixture was again heated to 74.5° C. and 286.2 kg ethanol (5% 2-propanol) were added within 3 hours while maintaining the temperature between 70 and 80° C. The mixture was cooled to 71° C. and stirred for 13 hours and 37 minutes while keeping the temperature between 65 and 75° C. Then the mixture was cooled to 59.9° C. and the crystals were separated by centrifugation. The crystals on the centrifuge were washed with a mixture of 38.0 kg ethanol (5% 2-propanol) and 6.9 kg water via the crystallization vessel and directly via a CIP (cleaning in place) pipe with a mixture of 38.1 kg ethanol (5% 2-propanol) and 6.9 kg water followed by 43.8 kg ethanol (5% 2-propanol). After separation of the washing liquids by centrifugation, the crystals were transferred into a dryer and dried for 12 hours and 7 min. at 50° C. under vacuum (101 mbar) using a nitrogen flow of 500 L/min. A sample was taken to measure the content of residual solvents. The water content of the sample was 0.49% w/w and the content of ethanol was 0.04% w/w. No 2-propanol was detected. 22.98 kg of crystalline monosodium salt of 5-methyl-(6S)-tetrahydrofolic acid (assay 5-methyltetrahydrofolic acid 97.9% w/w) were removed from the dryer, corresponding to an assay corrected yield of 75.9%.

Example 16: Solubility of the Crystalline Monosodium Salt of 5-methyl-(6S)-tetrahydrofolic Acid The solubility of the crystalline monosodium salt of 5-methyl-(6S)-tetrahydrofolic acid in water was measured by determining the concentration of 5-methyl-(6S)-tetrahydrofolic acid in the supernatant liquid after having stirred a suspension of crystalline monosodium salt of 5-methyl-(6S)-tetrahydrofolic acid in water for 30 minutes, always keeping an excess of solid material at the bottom of the flask.

The solubility of the crystalline monosodium salt of 5-methyl-(6S)-tetrahydrofolic acid in water at room temperature was 9.3 mg/ml (equivalent to 9.6 mg/ml of the calcium salt of 5-methyl-(6S)-tetrahydrofolic acid).

The solubility of the crystalline calcium salt of 5-methyl-(6S)-tetrahydrofolic acid in water measured under the same conditions was 7.1 mg/ml.

Reference Example 17: Preparation of the Amorphous Monosodium Salt of 5-methyl-(6S)-tetrahydrofolic Acid 6.0 g of crystalline 5-methyl-(6S)-tetrahydrofolic acid monosodium salt were added at room temperature to 600 g water. Solids were removed by suction filtration. The filtrate was frozen in a bath with liquid nitrogen and lyophilized in vacuum at 0.07 mbar. After 2 days the vacuum was replaced by nitrogen gas. 6.0 g amorphous 5-methyl-(6S)-tetrahydrofolic acid monosodium salt were obtained with a purity of 95.2% area, water content 8.8% w/w, assay sodium 4.5% w/w.

Example 18: Stability of the Crystalline Monosodium Salt of 5-methyl-(6S)-tetrahydrofolic Acid In order to compare the long-term stabilities of the crystalline monosodium salt of 5-methyl-(6S)-tetrahydrofolic acid, the compound of the invention, to the long-term stability of the crystalline calcium salt of 5-methyl-(6S)-tetrahydrofolic acid as prepared according to EP 1 044 975 B1, respective stability data has been generated at various temperatures and humidities.

Figure 7:
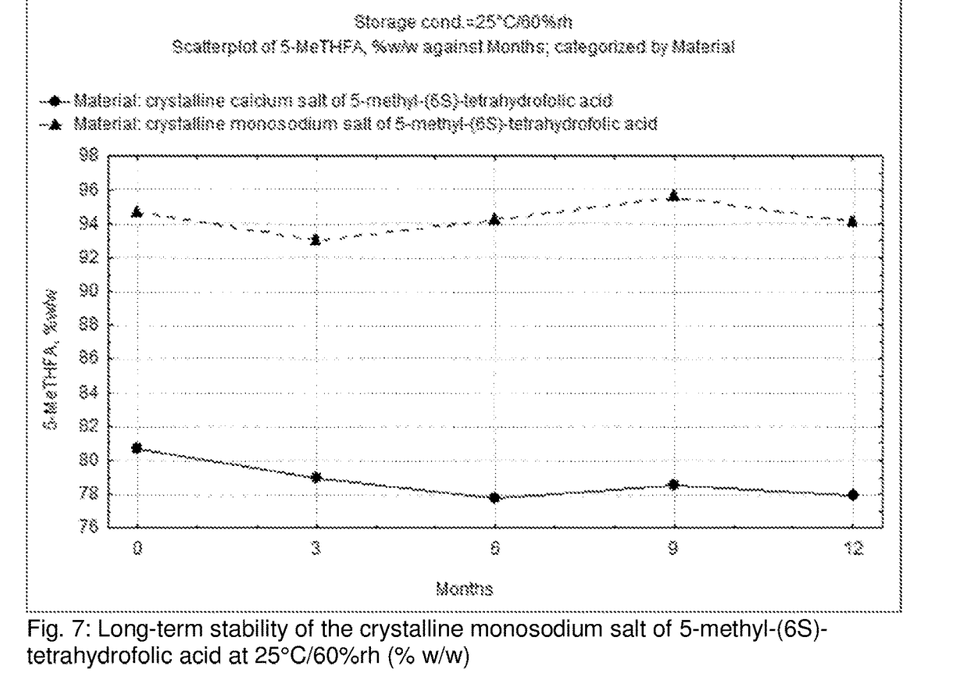
FIG. 7 shows the long-term stability of the crystalline monosodium salt of 5-methyl-(6S)-tetrahydrofolic acid at 25° C./60% rh (% w/w).
Figure 8:
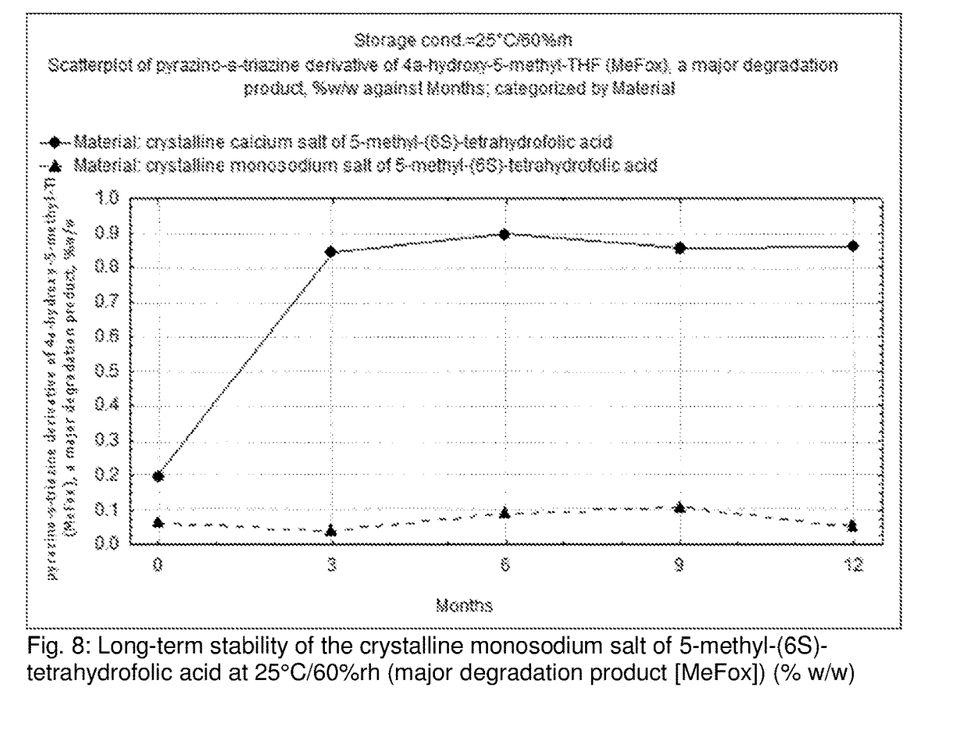
FIG. 8 shows the long-term stability of the crystalline monosodium salt of 5-methyl-(6S)-tetrahydrofolic acid at 25° C./60% rh (major degradation product [MeFox]) (% w/w).

(a) Stability of the Crystalline Monosodium Salt of 5-methyl-(6S)-tetrahydrofolic Acid at 25° C./60% rh Crystalline calcium salt of 5-methyl-(6S)-tetrahydrofolic acid, prepared according to literature procedures (EP 1 044 975 B1) and crystalline monosodium salt of 5-methyl-(6S)-tetrahydrofolic acid, prepared as disclosed in Example 15, were stored at 25° C./60% rh. The content of 5-methyl-(6S)-tetrahydrofolic acid remaining in the samples was measured by HPLC at periodic intervals (% w/w). The results are shown in Table 3a and FIG. 7. The content of 5-methyl-(6S)-tetrahydrofolic acid remaining was also compared to the initial value at the time of preparation (% rel.). The results are shown in Tables 3b. Additionally the content of the pyrazino-s-triazine derivative of 4α-hydroxy-5-methyl-THF (MeFox), a major degradation product, was measured by HPLC at periodic intervals and disclosed as absolute values (% w/w). The results are shown in Table 4 and FIG. 8.

TABLE 3a

Long-term stability of the crystalline monosodium salt of 5-methyl-(6S)-tetrahydrofolic acid at 25° C./60% rh (% w/w)

| | 5-methyl-(6S)-tetrahydrofolic acid (% w/w) | | | | |
| --- | --- | --- | --- | --- | --- |
| | 0 months | 3 months | 6 months | 9 months | 12 months |
| crystalline monosodium salt of 5-methyl-(6S)-tetrahydrofolic acid | 94.7 | 93.0 | 94.2 | 95.6 | 94.1 |
| crystalline calcium salt of 5-methyl-(6S)-tetrahydrofolic acid | 80.7 | 79.0 | 77.7 | 78.5 | 77.9 |

TABLE 3b

Long-term stability of the crystalline monosodium salt of 5-methyl-(6S)-tetrahydrofolic acid at 25° C./60% rh (% rel.)

| | 5-methyl-(6S)-tetrahydrofolic acid (% rel.) | | | | |
| --- | --- | --- | --- | --- | --- |
| | 0 months | 3 months | 6 months | 9 months | 12 months |
| crystalline monosodium salt of 5-methyl-(6S)-tetrahydrofolic acid | 100.0 | 98.3 | 99.5 | 101.0 | 99.4 |
| crystalline calcium salt of 5-methyl-(6S)-tetrahydrofolic acid | 100.0 | 97.9 | 96.3 | 97.3 | 96.5 |

TABLE 4

Long-term stability of the crystalline monosodium salt of 5-methyl-(6S)-tetrahydrofolic acid at 25° C./60% rh (major degradation product [MeFox])

| | Pyrazino-s-triazine derivative of 4α-hydroxy-5-methyl-THF (MeFox) (% w/w) | | | | |
| --- | --- | --- | --- | --- | --- |
| | 0 months | 3 months | 6 months | 9 months | 12 months |
| crystalline monosodium salt of 5-methyl-(6S)-tetrahydrofolic acid | 0.06 | 0.04 | 0.09 | 0.11 | 0.05 |
| crystalline calcium salt of 5-methyl-(6S)-tetrahydrofolic acid | 0.20 | 0.84 | 0.90 | 0.85 | 0.86 |

TABLE 4-continued

Long-term stability of the crystalline monosodium salt of 5-methyl-(6S)-tetrahydrofolic acid at 25° C./60% rh (major degradation product [MeFox])

| | Pyrazino-s-triazine derivative of 4α-hydroxy-5-methyl-THF (MeFox) (% w/w) | | | | |
| --- | --- | --- | --- | --- | --- |
| | 0 months | 3 months | 6 months | 9 months | 12 months |
| (6S)-tetrahydrofolic acid | | | | | |

Figure 9:
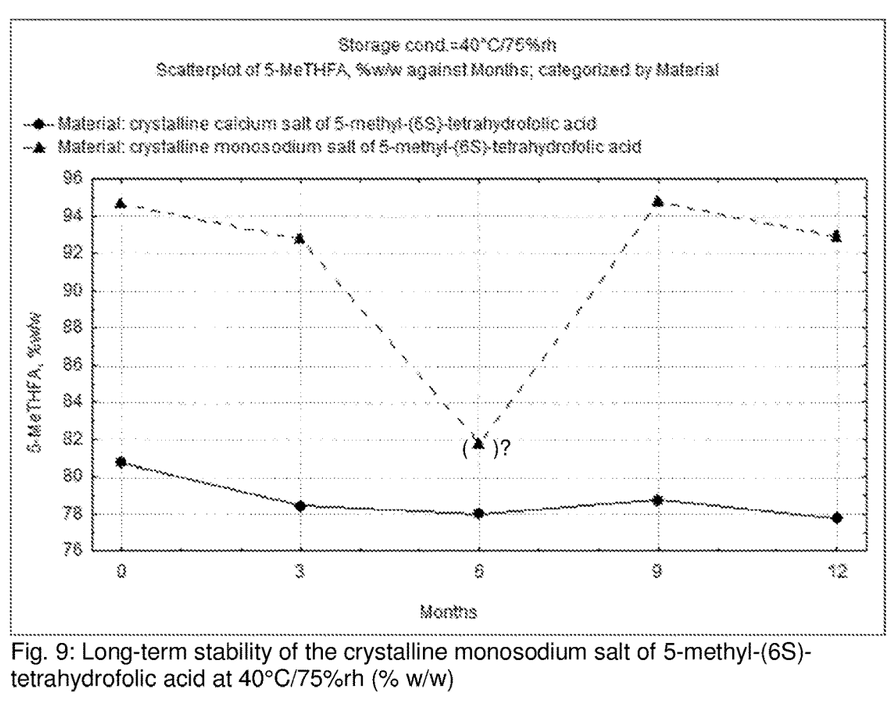
FIG. 9 shows the long-term stability of the crystalline monosodium salt of 5-methyl-(6S)-tetrahydrofolic acid at 40° C./75% rh (% w/w).
Figure 10:
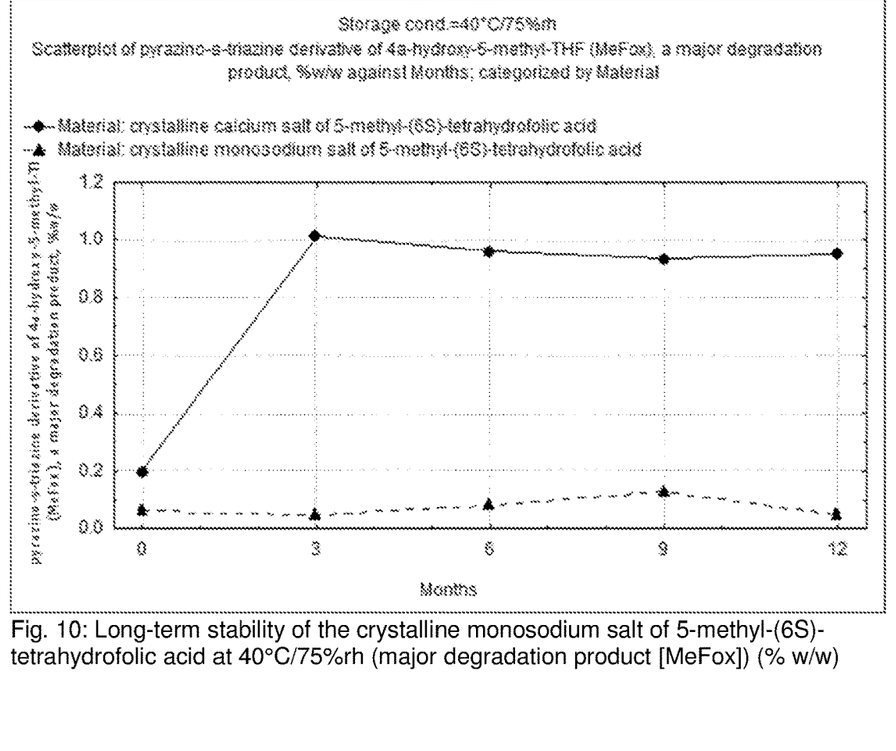
FIG. 10 shows the long-term stability of the crystalline monosodium salt of 5-methyl-(6S)-tetrahydrofolic acid at 40° C./75% rh (major degradation product [MeFox]) (% w/w).

(b) Stability of the Crystalline Monosodium Salt of 5-methyl-(6S)-tetrahydrofolic Acid at 40° C./75% rh Crystalline calcium salt of 5-methyl-(6S)-tetrahydrofolic acid, prepared according to literature procedures (EP 1 044 975 B1) and crystalline monosodium salt of 5-methyl-(6S)-tetrahydrofolic acid, prepared as disclosed in Example 15, were stored at 40° C./75% rh. The content of 5-methyl-(6S)-tetrahydrofolic acid remaining in the sample was measured by HPLC at periodic intervals (% w/w). The results are shown in Table 5a and FIG. 9. The content of 5-methyl-(6S)-tetrahydrofolic acid remaining was also compared to the initial value at the time of preparation (% rel.). The results are shown in Tables 5b. Additionally the content of the pyrazino-s-triazine derivative of 4α-hydroxy-5-methyl-THF (MeFox), a major degradation product, was measured by HPLC at periodic intervals and disclosed as absolute values (% w/w). The results are shown in Table 6 and FIG. 10.

TABLE 5a

Long-term stability of the crystalline monosodium salt of 5-methyl-(6S)-tetrahydrofolic acid at 40° C./75% rh (% w/w)

| | 5-methyl-(6S)-tetrahydrofolic acid (% w/w) | | | | |
| --- | --- | --- | --- | --- | --- |
| | 0 months | 3 months | 6 months | 9 months | 12 months |
| crystalline monosodium salt of 5-methyl-(6S)-tetrahydrofolic acid | 94.7 | 92.7 | (81.8)[1] | 94.8 | 92.9 |
| crystalline calcium salt of 5-methyl-(6S)-tetrahydrofolic acid | 80.7 | 78.5 | 78.0 | 78.8 | 77.8 |

[1]Most likely lab error

TABLE 5b

Long-term stability of the crystalline monosodium salt of 5-methyl-(6S)-tetrahydrofolic acid at 40° C./75% rh (% rel.)

| | 5-methyl-(6S)-tetrahydrofolic acid (% rel.) | | | | |
| --- | --- | --- | --- | --- | --- |
| | 0 months | 3 months | 6 months | 9 months | 12 months |
| crystalline monosodium salt of 5-methyl-(6S)-tetrahydrofolic acid | 100.0 | 98.0 | (86.4)[1] | 100.1 | 98.2 |
| crystalline calcium salt of 5-methyl-(6S)-tetrahydrofolic acid | 100.0 | 97.2 | 96.6 | 97.6 | 96.3 |

[1]Most likely lab error

TABLE 6

Long-term stability of the crystalline
monosodium salt of 5-methyl-(6S)-tetrahydrofolic
acid at 40° C./75% rh (major degradation product [MeFox])

| | Pyrazino-s-triazine derivative of 4α-hydroxy-5-methyl-THF (MeFox) (% w/w) | | | | |
|---|---|---|---|---|---|
| | 0 months | 3 months | 6 months | 9 months | 12 months |
| crystalline monosodium salt of 5-methyl-(6S)-tetrahydrofolic acid | 0.06 | 0.05 | 0.08 | 0.13 | 0.05 |
| crystalline calcium salt of 5-methyl-(6S)-tetrahydrofolic acid | 0.20 | 1.01 | 0.96 | 0.93 | 0.95 |

Tables 3 to 6 with the stability data of crystalline monosodium salt of 5-methyl-(6S)-tetrahydrofolic acid as disclosed in in the present invention clearly shows that i) there is a remarkable difference in the stability of crystalline monosodium salt of 5-methyl-(6S)-tetrahydrofolic acid compared to the crystalline calcium salt of 5-methyl-(6S)-tetrahydrofolic acid and ii) the crystalline monosodium salt of 5-methyl-(6S)-tetrahydrofolic acid is much more stable over a long period of time than crystalline calcium salt of 5-methyl-(6S)-tetrahydrofolic acid.

The invention claimed is:

1. A crystalline sodium salt of 5-methyl-(6S)-tetrahydrofolic acid of the following formula having a molar ratio of 5-methyl-(6S)-tetrahydrofolic acid to sodium from 1:0.5 to 1:1.5.

2. The crystalline salt of claim 1, wherein the molar ratio of 5-methyl-(6S)-tetrahydrofolic acid to sodium is from 1:0.75 to 1:1.25.

3. The crystalline salt of claim 1, wherein
   the molar ratio of 5-methyl-(6S)-tetrahydrofolic acid to sodium is 1:1 or
   which is a monosodium salt of 5-methyl-(6S)-tetrahydrofolic acid.

4. The crystalline salt of claim 1, having at least 99% or more chemical and stereoisomerical purity.

5. A food additive, comprising the crystalline sodium salt of 5-methyl-(6S)-tetrahydrofolic acid according to claim 1 and one or more acceptable excipients.

6. A vitamin composition, comprising the crystalline sodium salt of 5-methyl-(6S)-tetrahydrofolic acid according to claim 1 and one or more acceptable excipients.

7. A pharmaceutical composition, comprising the crystalline sodium salt of 5-methyl-(6S)-tetrahydrofolic acid according to claim 1 and one or more pharmaceutically acceptable excipients.

8. The pharmaceutical composition according to claim 7, wherein the pharmaceutical composition is a tablet, a capsule, an oral liquid preparation, a powder, a lyophilisate, a granule, a lozenge, a reconstitutable powder, an injectable or infusable solution or suspension or a suppository.

9. The pharmaceutical composition according to claim 7, wherein the pharmaceutical composition is formulated for oral, parenteral, intramuscular, intraspinal, intrathecal, peridontal, topical or rectal administration.

10. The pharmaceutical composition according to claim 7, wherein the pharmaceutical composition further comprises at least one additional therapeutic agent.

11. A method for treating a disease or condition selected from the group consisting of anemia, neural tube defects, cardiovascular diseases, depression, cognitive impairment, Alzheimer's disease, osteoporosis, dietary management of low plasma, low red blood cell folate, low cerebrospinal fluid folate, low peripheral nervous system folate, and central nervous system folate by homocysteine-lowering, comprising administering to a patient in need thereof an effective amount of the crystalline sodium salt of 5-methyl-(6S)-tetrahydrofolic acid according to claim 1.

12. A process for synthesizing the crystalline sodium salt of 5-methyl-(6S)-tetrahydrofolic acid according to claim 1, comprising the steps of:
   a) providing of 5-methyl-(6S)-tetrahydrofolic acid, optionally in a solvent or a mixture of solvents;

b) adding sodium hydroxide to the composition of step a);
c) optionally adding a solvent, a mixture of solvents and/or a co-salt former to the composition of step b), or adding the composition of step b) to a solvent, a mixture of solvents and/or a co-salt former;
d) crystallizing;
e) optionally adding more solvent or mixture of solvents; and
f) isolating the obtained solid.

13. The process of claim 12, wherein 5-methyl-(6S)-tetrahydrofolic acid and sodium hydroxide in step b) are present at a molar ratio of 1:0.5 to 1:1.5.

14. The process of claim 12, wherein the molar ratio of 5-methyl-(6S)-tetrahydrofolic acid to the co-salt former in the composition provided in step c) is in the range of 1:0.5 to 1:3.

15. The process of claim 12, wherein the solvent in step (a), step (c) or step (e) or in a combination thereof is selected from the group consisting of water, water-soluble alcohols, methanol, ethanol, isopropanol, n-propanol, acetonitrile, tetrahydrofuran, acetone, methyl ethyl ketone, methyl isobutyl ketone, and benzylalcohol, or is a mixture thereof.

16. The process of claim 12, wherein the co-salt former in step c) is an organic base with a pKa value from 6 to 11.

17. The process of claim 12, wherein the co-salt former in step c) is an organic base with a pKa value from 7 to 10.

18. The process of claim 12, wherein the co-salt former in step c) is selected from the group consisting of 4-(2-hydroxyethyl)-morpholine, 1-(2-hydroxyethyl)-pyrrolidine, imidazole, 2-dimethylaminoethanol, and Cert-butylamine; or is a mixture thereof.

19. The process of claim 12, wherein the co-salt former in step c) is 4-(2-hydroxyethyl)morpholine.

20. The process of claim 12, wherein the temperature in step d) is at least 30° C.

21. The process of claim 12, wherein the process further comprises adding seed crystals in step (a), step (b), step (c) or step (d) or in a combination thereof.

22. A process for producing the pharmaceutical composition, wherein the process comprises adding the crystalline sodium salt according to claim 1 to the one or more pharmaceutically acceptable excipients.

* * * * *